(12) United States Patent
Ellis et al.

(10) Patent No.: US 10,787,659 B2
(45) Date of Patent: Sep. 29, 2020

(54) METHODS AND COMPOSITIONS FOR NUCLEIC ACID ISOLATION

(71) Applicant: LIFE TECHNOLOGIES AS, Carlsbad, CA (US)

(72) Inventors: Darren Ellis, Lommedalen (NO); Hannah Lindstroem, Oslo (NO)

(73) Assignee: LIFE TECHNOLOGIES AS, Oslo (NO)

( * ) Notice: Subject to any disclaimer, the term of this patent is extended or adjusted under 35 U.S.C. 154(b) by 12 days.

(21) Appl. No.: 16/137,448

(22) Filed: Sep. 20, 2018

(65) Prior Publication Data

US 2019/0024077 A1    Jan. 24, 2019

Related U.S. Application Data

(63) Continuation of application No. PCT/EP2017/057253, filed on Mar. 28, 2017.

(60) Provisional application No. 62/315,587, filed on Mar. 30, 2016.

(51) Int. Cl.
*C12N 15/10* (2006.01)

(52) U.S. Cl.
CPC .................................. *C12N 15/1003* (2013.01)

(58) Field of Classification Search
CPC ....................... C12N 15/1003; C12Q 2527/125
See application file for complete search history.

(56) References Cited

U.S. PATENT DOCUMENTS

| | | | | |
|---|---|---|---|---|
| 5,346,994 | A | 9/1994 | Chomczynski | |
| 6,777,182 | B2 * | 8/2004 | Baban | C12Q 1/6883 435/6.17 |
| 7,794,932 | B2 | 9/2010 | Chomczynski | |
| 8,148,061 | B2 * | 4/2012 | Baban | C12Q 1/6883 435/6.18 |
| 8,367,817 | B2 * | 2/2013 | Chomczynski | C12N 15/1003 536/25.41 |
| 8,581,038 | B2 * | 11/2013 | Lagudah | C07K 14/415 800/279 |
| 9,115,370 | B2 * | 8/2015 | Lagudah | C07K 14/415 |
| 9,309,559 | B2 * | 4/2016 | Loudig | C12O 1/6806 |

| | | |
|---|---|---|
| 2012/0042410 A1 | 2/2012 | Lee et al. |
| 2012/0208869 A1 | 8/2012 | Baban et al. |
| 2014/0101791 A1 | 4/2014 | Lagudah et al. |
| 2014/0308670 A1 | 10/2014 | Loudig et al. |

FOREIGN PATENT DOCUMENTS

| | | |
|---|---|---|
| WO | 1998/045311 | 10/1998 |
| WO | 2005/103252 | 11/2005 |
| WO | 2012/083198 | 6/2012 |
| WO | 2017/167716 | 10/2017 |

OTHER PUBLICATIONS

Brawerman et al., A procedure for the isolation of mammalian messenger ribonucleic acid, *Biochemistry*, vol. 11, No. 4, Feb. 1972, 637-641.

Chomczynski et al., Single-step method of RNA isolation by acid guanidinium thiocyanate-phenol-chloroform extration, *Analytical Biochemistry*, vol. 162, No. 1, Apr. 1987, 156-159.

Chomczynski et al., Substitution of Chloroform by Bromochloropropane in the Single-Strep Method of RNA Isolation, *Analytical Biochemistry*, vol. 225, 1995, 163-164.

Palmiter, Magnesium precipitation of ribonucleoprotein complexes. Expedient techniques for the isolation of undegraded polysomes and messenger ribonuceotide acid, *Biochemistry*, vol.13, No. 17, 1973, 3606-3615.

PCT/EP2017/057253, International Preliminary Report on Patentability, dated Oct. 11, 2018, 1-6.

Perry et al, The production of ribosomal RNA from high molecular weight precursors : III. Hydrolysis of pre-ribosomal and ribosomal RNA by a 3'-OH specific exoribonuclease, *Journal of Molecular Biology*, vol. 70, No. 2, Sep. 1972, 265-279.

PCT/EP2017/057253, International Search Report & Written Opinion dated Jun. 7, 2017, 1-10.

* cited by examiner

*Primary Examiner* — Lawrence E Crane

(57) ABSTRACT

The disclosure generally relates to compositions and methods for the extraction of nucleic acids from biological samples. In particular embodiments the extraction involves mixing dibromochloromethane, iodochloromethane or mixtures thereof with a biological sample that has been mixed with a phenol-based extraction solution. Centrifugation of the sample is not needed to achieve phase separation which occurs using the present methods in as little as one to two minutes with no phenol carryover.

20 Claims, 3 Drawing Sheets

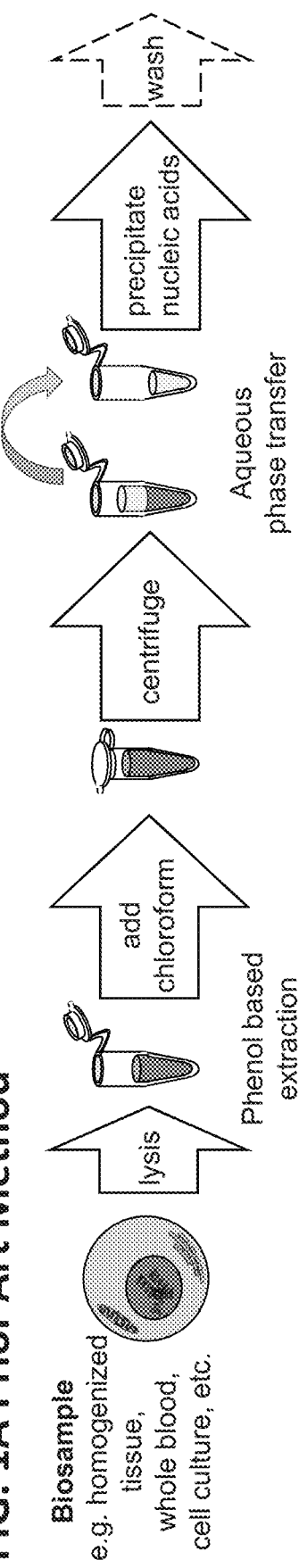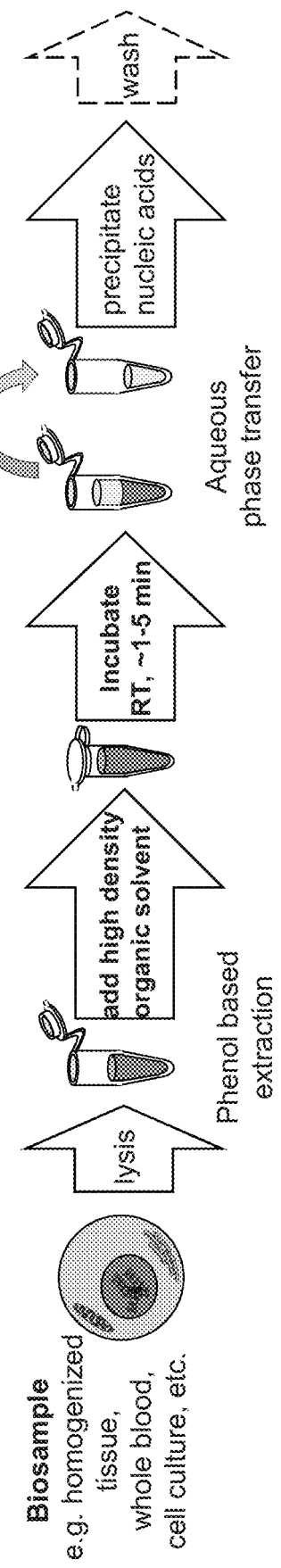

METHODS AND COMPOSITIONS FOR NUCLEIC ACID ISOLATION

CROSS REFERENCE

This Application is a continuation application under 35 U.S.C. § 120 of pending International Application No. PCT/EP2017/057253 filed Mar. 28, 2017 which application claims the benefit under 35 U.S.C. § 119(e) of U.S. Provisional Application No. 62/315,587 filed Mar. 30, 2016. The entire contents of the aforementioned applications are incorporated by reference herein.

FIELD OF THE INVENTION

The disclosure generally relates to methods and compositions for the extraction of nucleic acids from biological samples. In some aspects, the invention allows for the extraction of nucleic acid molecules without a centrifugation step.

BACKGROUND

Solutions of guanidinium and phenol commonly have been used to extract nucleic acids and proteins from complex biological samples. The method described by Chomczynski and Sacchi (Anal. Biochem. 162: 156-159; 1987) has been considered the standard for RNA isolation since its introduction in 1987. These methods rely on the differential partitioning of nucleic acids between the aqueous and organic phases which requires the separation of the phases by centrifugation. While effective for the isolation of nucleic acids from biological samples, the centrifugation step makes these methods tedious when processing large numbers of samples, and difficult to automate. A first aspect of the present invention is to provide a method of nucleic acid isolation which lacks a centrifugation step and is more adaptable to automation. A second aspect of the present invention is to provide alternative organic solvents that are less toxic and reduce health risks of exposed users.

SUMMARY OF THE INVENTION

The invention relates, in part, to compositions and methods for the isolation of nucleic acids from biological samples. Some embodiments relate to a method for extraction of nucleic acids from a biological sample. Such a method may comprise a) adding an extraction solution to a biological sample, b) mixing the solution until the sample is thoroughly dissolved, c) adding an organic solvent to the extraction solution, d) vigorously mixing the extraction solution, e) allowing the extraction solution to stand and f) removing the upper aqueous phase containing the nucleic acid. In additional embodiments, the method may further comprise: g) processing the aqueous phase by one or more of alcohol precipitation, anion exchange chromatography, silica based chromatography, bead based protocols, treatment with DNAse and/or treatment with RNAse. In some embodiments, the extraction solution may further comprise a chaotropic agent such as guanidinium or a guadinium salt. In other embodiments thiocyanate compounds such as ammonium thiocyanate or sodium thiocyanate may also be included in the extraction solution.

In some embodiments the pH of the extraction solution may be controlled using a buffer allowing for the differential partitioning of the DNA and RNA. In these embodiments the pH may be between 3.5 and 8. In one method embodiment, the pH of the extraction solution is below 5.

In other embodiments the extraction solution may further comprise a solubilization reagent such as glycerol.

In many embodiments, the organic solvent has a density that is greater than or at least about 1.9 g/cm$^3$, the melting point of the solvent is less than or equal to about 15° C. and the boiling point of the solvent is greater than about 50° C. In some aspects the organic solvent may be a halo substituted straight chain alkyl compound. In particular embodiments the organic solvent may be dibromochloromethane, dibromomethane, iodochloromethane, 1,3-dibromopropane, 1,2-dibromopropane or 1,3-diiodopropane.

In some aspects, the invention relates to a composition comprising: a) a biological sample, b) a phenol based extraction solution and c) an organic solvent having a density that is greater than or at least about 1.9 g/cm$^3$ with a melting point of less than or equal to 15° C. and a boiling point greater than about 50° C. In some embodiments the solvent density may be greater than or at least about 2.0 g/cm$^3$ and in further embodiments the density may be greater than or at least about 2.4 g/cm$^3$. In specific embodiments, the extraction solution may further comprise a chaotropic agent such as guanidinium or a guadinium salt. In other embodiments thiocyanate compounds such as ammonium thiocyanate or sodium thiocyanate may also be included in the extraction solution. In further embodiments the pH of the extraction solution may be controlled using a buffer allowing for the differential partitioning of the DNA and RNA. In these embodiments the pH may be between 3.5 and 8, or below 5. In other embodiments the extraction solution may further comprise a solubilization reagent such as glycerol.

A method for the extraction of nucleic acid molecules from a biological sample comprising the following steps a)-d) is an aspect of embodiments herein: a) mixing the biological sample and a phenol-based extraction solution to form a dissolved sample, b) mixing an organic solvent with the dissolved sample to form a mixture, wherein the organic solvent is a halo-substituted alkyl compound where the alkyl has one to three carbon atoms, the organic solvent has a density at room temperature of greater than or at least about 1.9 g/cm$^3$ and wherein the organic solvent has a melting point of less than or equal to 15° C., c) allowing the mixture to stand for an amount of time to achieve separation of an aqueous phase and an organic phase; and d) removing the aqueous phase containing the nucleic acid. In one embodiment of the above method, steps a)-d) are performed without a centrifugation step. In another aspect of the above method, the method consists of steps a)-d).

A method for the extraction of nucleic acid molecules from a biological sample comprising the following steps a)-d) is an aspect of embodiments herein: a) mixing the biological sample and a phenol-based extraction solution to form a dissolved sample, b) mixing an organic solvent with the dissolved sample to form a mixture, wherein the organic solvent is a halo-substituted alkyl compound where the alkyl has one to three carbon atoms, the organic solvent has a density at room temperature of greater than or at least about 2.0 g/cm$^3$ and, optionally, greater than or at least about 2.4 g/cm$^3$, wherein the organic solvent has a melting point of less than or equal to 15° C., c) allowing the mixture to stand for an amount of time to achieve separation of an aqueous phase and an organic phase; and d) removing the aqueous phase containing the nucleic acid. In one embodiment of the above method, steps a)-d) are performed without a centrifugation step. In another aspect of the above method, the method consists of steps a)-d).

In an aspect of the above methods, the amount of time to allow the mixture to stand to achieve separation of the aqueous phase and the organic phase is about 40 sec, about 1 min, about 2 min, about 5 min, or about 15 min.

In an aspect of the above methods, the organic solvent has a density that is ≥1.9 g/cm$^3$ and <4.0 g/cm$^3$, or ≥2.0 g/cm$^3$ and <4.0 g/cm$^3$, or ≥2.4 g/cm$^3$ and <4.0 g/cm$^3$ selected from those listed in Table 1 or Table 2, or a mixture thereof. In an aspect of the above methods, the organic solvent has a density that is ≥1.9 g/cm$^3$ and ≤3.3 g/cm$^3$, or ≥2.0 g/cm$^3$ and ≤3.3 g/cm$^3$, or ≥2.4 g/cm$^3$ and ≤3.3 g/cm$^3$ selected from those listed in Table 1 or Table 2, or a mixture thereof. In another aspect of the above methods, the organic solvent has a density that is ≥1.9 g/cm$^3$ and <3.3 g/cm$^3$, or ≥2.0 g/cm$^3$ and <3.3 g/cm$^3$, or ≥2.4 g/cm$^3$ and <3.3 g/cm$^3$ selected from those listed in Table 1 or Table 2, or a mixture thereof.

In an aspect of the above methods, the organic solvent is chloroiodomethane (also written as iodochloromethane), dibromochloromethane, 1,3 diiodopropane, bromoform, 1,1,2,2, tetrabromoethane, or a mixture thereof. In another aspect of the above methods, the organic solvent is 1,2 dibromopropane, 1,3 dibromopropane, chloroiodomethane (also written as iodochloromethane), dibromochloromethane, 1,3 diiodopropane, bromoform, 1,1,2,2, tetrabromoethane, diiodomethane, or a mixture thereof. In another aspect of the above methods, the organic solvent is chloroiodomethane (also written as iodochloromethane), dibromochloromethane, or a mixture thereof.

BRIEF DESCRIPTION OF THE FIGURES

FIG. 1A shows a common extraction workflow with a centrifugation step and FIG. 1B shows an improved extraction workflow according to methods presented herein.

DETAILED DESCRIPTION OF THE INVENTION

Definitions

Figure 2:
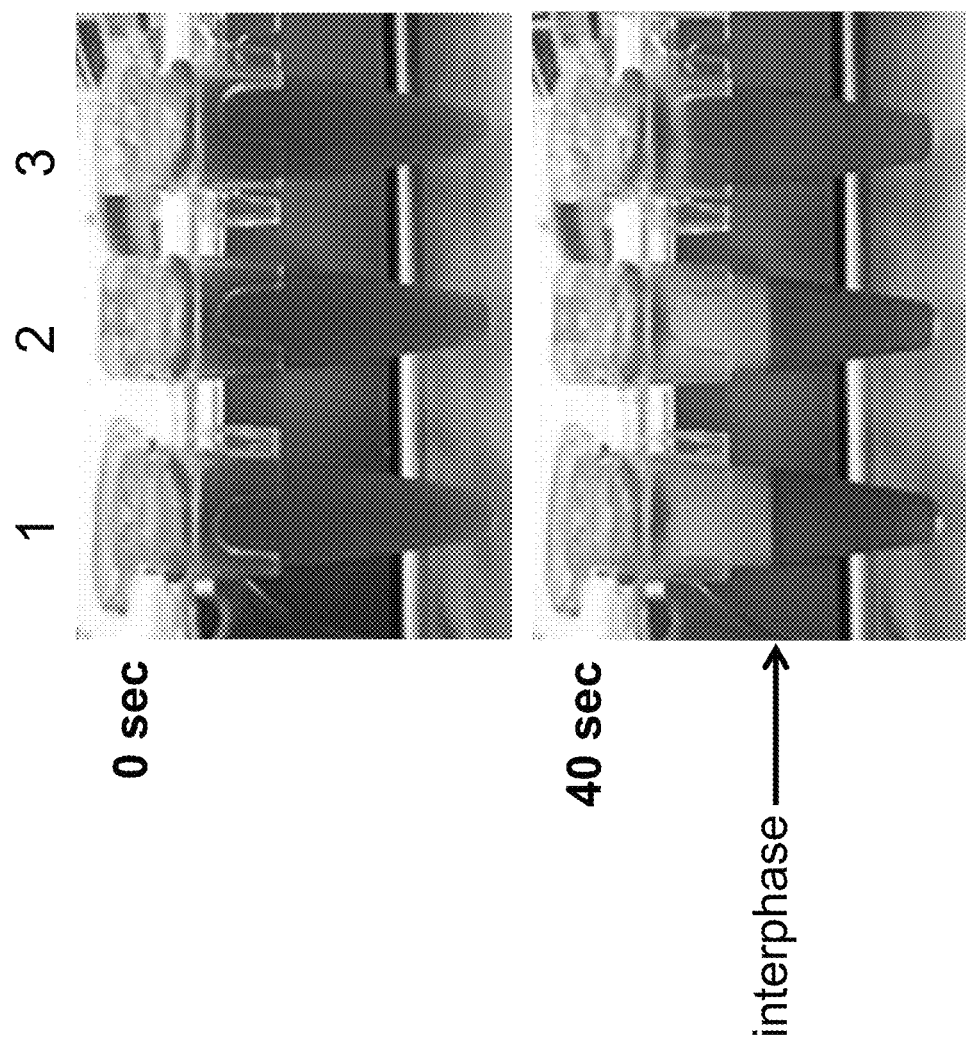
FIG. 2 shows photographs of extraction samples comprising different organic solvents taken immediately after vortexing (upper image) or after 40 seconds (lower image). Phase separation achieved by standing for 40 seconds is reflected by the formation of an interphase highlighted by an arrow. Sample 1) dibromochloromethane sample 2) bromoform, sample 3) chloroform.

Nucleic Acid Molecule: As used herein the term "nucleic acid molecule" refers to a covalently linked sequence of nucleotides or bases (e.g., ribonucleotides for RNA and deoxyribonucleotides for DNA but also include DNA/RNA hydrids where the DNA is in separate strands or in the same strands) in which the 3' position of the pentose of one nucleotide is joined by a phosphodiester linkage to the 5' position of the pentose of the next nucleotide. Nucleic acid molecule may be single- or double-stranded or partially double-stranded. Nucleic acid molecule may appear in linear or circularized form in a supercoiled or relaxed formation with blunt or sticky ends and may contain "nicks". Nucleic acid molecule may be composed of completely complementary single strands or of partially complementary single strands forming at least one mismatch of bases. Nucleic acid molecule may further comprise two self-complementary sequences that may form a double-stranded stem region, optionally separated at one end by a loop sequence. The two regions of nucleic acid molecule which comprise the double-stranded stem region are substantially complementary to each other, resulting in self-hybridization. However, the stem can include one or more mismatches, insertions or deletions.

Nucleic acid molecules may comprise chemically, enzymatically, or metabolically modified forms of nucleic acid molecules or combinations thereof. Nucleic acid molecule also refers to short nucleic acid molecules, often referred to as, for example, primers or probes. Primers are often referred to as single-stranded starter nucleic acid molecules for enzymatic assembly reactions whereas probes may be typically used to detect at least partially complementary nucleic acid molecules. A nucleic acid molecule has a "5'-terminus" and a "3'-terminus" because nucleic acid molecule phosphodiester linkages occur between the 5' carbon and 3' carbon of the pentose ring of the substituent mononucleotides. The end of a nucleic acid molecule at which a new linkage would be to a 5' carbon is its 5' terminal nucleotide. The end of a nucleic acid molecule at which a new linkage would be to a 3' carbon is its 3' terminal nucleotide. A terminal nucleotide or base, as used herein, is the nucleotide at the end position of the 3'- or 5'-terminus. A nucleic acid molecule sequence, even if internal to a larger nucleic acid molecule (e.g. a sequence region within a nucleic acid molecule), also can be said to have 5'- and 3'-ends.

The term "melting point" as used herein generally refers to the temperature at which the solid and liquid forms of the compound exist in equilibrium at atmospheric pressure equivalent to 760 mmHg.

The term "room temperature" as used herein means the ambient temperature at typical laboratory conditions which is typically between about 20° C. to about 25° C. Room temperature (or "RT" as used in the examples) may therefore refer to a temperature range or to specific temperature values within that range, such as e.g. 20° C., 21° C. or 25° C. In certain instances, room temperature is equal to 25° C.

The term "density" as used herein refers to the mass density of a material, and is defined as its mass per unit volume. Volume may be expressed in cubic centimeter (cm$^3$) or milliliter (mL). Therefore, density may likewise be expressed in units of gram per cubic centimeter (g/cm$^3$) or units of gram per milliliter (g/mL). To determine the density of an organic solvent, both mass and volume of the solution need to be measured. The density of a substance varies with both temperature and pressure. Increasing the pressure on a solvent decreases its volume and thus increases its density whereas increasing the temperature of a substance decreases its density by increasing its volume. However, such variation is typically small for liquids when measured under standard laboratory conditions, i.e. at atmospheric pressure and at room temperature. Density values described in the literature for a certain substance may slightly vary depending on the specific conditions under which they were determined. For example, the density value for an organic solvent may be slightly higher when measured at 20° C. or 21° C. than when measured at 25° C. Different density values for the organic solvent Bromodichloromethane can be found in the literature ranging from 1.93 g/cm$^3$ to 1.99 g/cm$^3$. Thus the skilled person would understand that a density value of "about" or "at least about "2.0 g/cm$^3$" as used herein may include slight deviations of plus/minus 0.1 g/cm$^3$ and may therefore encompass Bromodichloromethane, whereas a definition of "greater than" or "at least" 2.0 g/cm³ would not encompass Bromodichloromethane.

The term "boiling point" as used herein refers to the temperature at which the vapor pressure of the liquid equals the external pressure under ambient conditions of one atmosphere of pressure at sea level (i.e., the boiling point at 760 mmHg pressure).

Detailed Description

The invention relates in part to methods and compositions for the isolation of nucleic acids from biological samples. The method is based on the differential partitioning of nucleic acids between the organic and aqueous phases of a liquid-liquid extraction. Phenol is typically chosen as the organic phase for the extraction solution because it is immiscible with water and because it denatures polymers such as proteins and carbohydrates. Because of the polar nature of their phosphate backbones, nucleic acids remain in the aqueous phase while lipid compounds remain soluble in the phenol. Proteins and other polymers are precipitated by the phenol and remain at the interface of the two phases. Phenol may be present in the extraction solution at a concentration of 30%-50% by volume based on the total volume of the solution. In some embodiments the concentration may be 30%-35%, 35%-40%, 30%-40%, 40%-45%, 45%-50% or 40%-50%. In some embodiments, a phenol extraction mixture may be used for RNA extraction that contains from 50% up to 80% to 83% phenol, for example. Alternatively, phenol derivatives such as phenylethanol, propylene phenoxytol, thymol, or butylphenol, that are less toxic than phenol itself, may be present in the extraction solution.

The extraction solution may additionally comprise compounds which increase the stability of nucleic acids. Such compounds include chaotropic agents such as guanidinium and its various salts including guanidinium isothiocyanate, guanidinium thiocyanate and guandinium hydrochloride. Chaotropic agents such as guanidinium salts inhibit the activity of nucleases thereby enhancing the stability of nucleic acids. The guanidinium compounds may be present in the extraction solution at a concentration of 0.5 M to 2 M based on the total volume of the solution. In some embodiments the concentration is 0.5-1 M, 1-1.5 M or 1.5-2 M guanidinium.

Thiocyanate compounds such as ammonium thiocyanate, guanidinium thiocyanate or sodium thiocyanate may also be included in the extraction solution. Thiocyanate compounds may be present at a concentration of 0.1-0.6 M based on the total volume of the solution. In particular embodiments the concentration may be 0.1-0.2 M, 0.2-0.3 M, 0.3-0.4 M, 0.4-0.5 M or 0.5-0.6 M.

The extraction solution may further comprise a solubilizing agent such as glycerol to assure that phenol stays in solution. The concentration of the solubilizing reagent may be from 3%-10% by volume based on the total volume of the solution. In particular embodiments the solubilizing reagent may have a concentration of 3%-5%, 5%-7% or 7%-10%.

Partitioning of DNA and RNA into the aqueous phase can be controlled by varying the pH of the extraction solution (Brawerman et. al. Biochemistry 11 (4), 1972; Perry et al. J. Mol. Biol., 70: 265-279, 1972). At neutral or mildly alkaline pH both DNA and RNA partition into the aqueous phase (Bradley et al., Lecture Notes on Molecular Medicine, 2nd Edition, Oxford: Blackwell, 2001; Revest et al., Molecular Neuroscience, N.Y.: Springer, 1998). Because DNA is less acidic than RNA, as the pH of the extraction drops, DNA is increasingly retained in the organic phase. Use of acidic extraction conditions may be used to preferentially isolate RNA. The pH of the extraction solution may be maintained by the use of a buffer such as sodium acetate or sodium citrate. The buffer may be present at a concentration of 0.05 M-0.2 M based on the total volume of the solution. The pH of the extraction solution may be from 3.5 to 8. In specific embodiments the pH may be from 3.5-4, 4-5, 5-6, 6-8, 3.5-5 or 4-6.

Exemplary extraction solutions which may be used for embodiments of the invention are described in the art. For example, solutions for extracting total RNA from leaves or plant material are described in U.S. publication Nos. 2014/0101791 A1 (e.g. paragraph [0208]) or 2012/0042410 A1 (e.g. paragraph [0082]), and extraction of total RNA from human biopsy cells is described in U.S. publication No. 2012/0208869 A1 (e.g. paragraph [00239]). Monophasic solutions suitable for simultaneous extraction of RNA, DNA and protein from various samples including tissue are described in U.S. Pat. No. 5,346,994 or U.S. publication number 2014/0308670 A1 (e.g. paragraph [0066]) and the extraction solutions described in the referenced sections may be combined with one or more high density organic solvents described herein to replace chloroform in phase separation and are therefore incorporated herein by reference. Extraction solutions suitable for use in the invention are also available commercially. These include TRIZOL™ from Thermo Fisher Scientific, TRI REAGENT™ from Molecular Research Center, Inc. and QIAzol Lysis Reagent from Qiagen. Suitable extraction solutions using acidic phenol effective in removing DNA contamination are also described in U.S. Pat. No. 7,794,932, the contents of which are incorporated herein by reference.

While the partitioning of nucleic acids will occur with a simple phenol based extraction using solutions as described above, the process can be made more efficient with the inclusion of a solvent which may improve the partitioning properties of the organic phase. Chloroform has typically been used as it reduces the level of residual aqueous phase (Palmiter R. D., Biochemistry, 13: 3606-3615, 1974). Separation of the phases after extraction has typically required centrifugation in order to achieve a clean separation of the organic and aqueous phases. Centrifugation is a labor intensive step that slows the nucleic acid isolation process and makes processing a large number of samples in an automated fashion difficult or impossible. We have unexpectedly found that choosing a solvent having a higher density than chloroform to add to the phenol based extraction solution allows the phases to separate cleanly with simple standing. The properties for such a solvent include that it is miscible with phenol but immiscible with water. In addition the solvent may have a density greater than or at least about 1.9 g/cm³ when measured at room temperature (e.g. at 25° C.) and pressure of 760 mmHg. In some embodiments the solvent density may be greater than or at least about 2.0 g/cm³ and in further embodiments the density may be greater than or at least about 2.4 g/cm³. In addition to density, the solvent should have properties that allow it to work well under typical laboratory conditions where these properties are typically determined at room temperature and a pressure of 760 mmHg. Preferably, the solvent should be liquid at relevant lab temperatures and not be too viscous or evaporate too easily. For example, iodoform, a halo-substituted methane, has a density of 4 g/cm³ at room temperature, but a melting point of 118° C., and is therefore unworkable at standard laboratory conditions. Suitable solvents may therefore have a melting point of 15° C. or less and a boiling point of about 50° C. or more. There are a number of halo substituted alkyl compounds that have these physical properties. Examples of suitable solvents include but are not limited to those found in Table 1. The density values indicated in Table 1 were rounded to two significant digits.

TABLE 1

| Solvent | Molecular Formula | Density (g/cm$^3$) at 25° C. | Melting Point (° C.) | Boiling Point (° C.) |
| --- | --- | --- | --- | --- |
| Bromoform | CHBr$_3$ | 2.89 | 8 | 149 |
| Dibromochloromethane | CHBr$_2$Cl | 2.45 | −22 | 119 |
| Bromodichloromethane | CHBrCl$_2$ | 1.98 | −55 | 87 |
| Iodobromomethane | CH$_2$BrI | 2.93 | 1 | 138 |
| Diiodomethane | CH$_2$I$_2$ | 3.33 | 5 | 181 |
| Bromochloromethane | CH$_2$BrCl | 1.99 | −88 | 68 |
| Dibromomethane | CH$_2$Br$_2$ | 2.48 | −52 | 96 |
| Iodochloromethane | CH$_2$ClI | 2.42 | −57 | 108 |
| Dibromoethane | C$_2$H$_4$Br$_2$ | 2.18 | 8 | 131 |
| 1,1,2,2-tetrabromoethane | C$_2$H$_2$Br$_4$ | 2.97 | −1.1 | 119 |
| 1,3-dibromopropane | C$_3$H$_6$Br$_2$ | 1.99 | −34 | 167 |
| 1,2-dibromopropane | C$_3$H$_6$Br$_2$ | 1.94 | −55 | 140 |
| 1,3-diiodopropane | C$_3$H$_6$I$_2$ | 2.58 | −20 | 111 |

Another aspect addressed by the current invention is providing alternative high density organic solvents that are less toxic than chloroform thereby further reducing the health risks of exposed users. Such less hazardous solvents suitable for methods of the invention include but are not limited to dibromochloromethane, dibromomethane, iodochloromethane, 1,3-dibromopropane, 1,2-dibromopropane and 1,3-diiodopropane.

The solvent may be added to the extraction solution at a ratio of from 1 part solvent to 5 parts extraction solution to a ratio of 1 part solvent to 1 part extraction solution. In some embodiments, mixtures of suitable solvents may be added at equal or different ratios.

When the extraction procedure is complete and the aqueous phase containing the desired nucleic acid (DNA or RNA or both, depending on the conditions discussed above) has been collected, the nucleic acid may be isolated using a variety of standard protocols. Standard nucleic acid isolation protocols include alcohol precipitation, anion exchange chromatography, silica based column or membrane protocols and bead based protocols. Commercially available kits for nucleic acid isolation using these methods include the PURELINK™ Genomic DNA kit, PURELINK™ RNA Mini kit, MAGMAX™ MIRVANA™ Total RNA Isolation kit, DYNABEADS™ SILANE Viral NA Kit and DYNABEADS™ SILANE Genomic DNA Kit, DYNABEADS™ mRNA DIRECT™ Purification Kit, DYNABEADS™ mRNA Purification Kit (for mRNA purification from total RNA preps) and DYNABEADS™ Oligo d(T) available from Thermo Fisher Scientific and the QIAGEN Plasmid kit, QIAprep Miniprep kit, and EZ1 kit from Qiagen. A comparison of a standard extraction workflow relying on chloroform and centrifugation for phase separation is shown in FIG. 1A, whereas a workflow according to the methods of the invention using high density organic solvents in the absence of a centrifugation step is shown in FIG. 1B.

An exemplary method for extraction of nucleic acids from a biological sample would start with selecting the starting material. Nucleic acids may be extracted from a variety of biological samples including bacteria, cultured cells, tissues including animal and plant tissue, optionally homogenized, and various biological fluids such as blood, urine, saliva, semen, and spinal fluid. Depending on the source and type of the biological sample, the biological sample may be mixed with the extraction solution at a ratio of about 10 parts by weight of extraction solution to 1 part biological sample. The sample is then mixed (for example by vortexing) until the sample is thoroughly dissolved in the extraction solution. For some types of tissue, mechanical disruption of the tissue such as use of a dounce homogenizer, bead beating or a pipette may be needed to sufficiently or fully dissolve the sample.

Once dissolved, the organic solvent may be added to the extraction solution. The final concentration of the organic solvent in the extraction solution may be from about 20% to about 50%. In specific embodiments the organic solvent concentration may be more than 15%, such as e.g. 20%-30%, 20%-40%, 30%-40%, 30%-50% or 40%-50%. Following addition of the organic solvent the extraction solution may be mixed vigorously (e.g. by vortexing) for about ten seconds to about one minute optionally followed by further gentle mixing for from about one to about ten minutes. The mixing time may be dependent on the type of sample with cultured cells or blood-derived samples needing a relatively short mixing time (e.g. from about 10 seconds to a minute), whereas samples having a large amount of connective tissue may require longer mixing times (e.g. more than 1 minute, 2 to 5 minutes, 5 to 10 min. or more than 10 minutes etc.). When mixing is complete the extraction is allowed to stand (i.e. without applying any centrifugal force) for a sufficient amount of time to allow for the separation of phases which is typically indicated by the formation of a visible interphase (see FIG. 2). In some instances, the extraction solution is allowed to stand for up to one minute (e.g. at least about 30 seconds or about 40 seconds as demonstrated in FIG. 2) to achieve phase separation. In other instances, the extraction solution may be allowed to stand for more than one minute, such as e.g. between 30 and 90 seconds, 1 to 5 min, 2 to 10 min or 5 to 10 min. In cases where samples having a large amount of connective or fibrous tissue are used, the extraction solution may be allowed to stand for up to 15 min. The time required to achieve phase separation in the absence of a centrifugation step may depend on the type of biological sample and/or the organic solvent used. For example, the time required to achieve complete phase separation may at least to some extent depend on the density of the organic solvent. By way of illustration, dibromochloromethane having a density of 2.45 g/cm$^3$ may achieve an even faster phase separation than 1,2 dibromopropane having a density of 1.94 g/cm$^3$. Thus, in certain circumstances, fast separation (within 1 minute) may be achieved where organic solvents having a density of at least 2.0 g/cm$^3$ or at least 2.4 g/cm$^3$ are used.

As seen in FIG. 2 within 40 seconds of standing without centrifugation, a sharp phase separation has occurred in the extractions where dibromochloroform (1) or bromoform (2) were used as the organic solvent compared to the extraction where chloroform (3) was the organic solvent and no phase separation has occurred. The greater liquid density of exemplary solvents dibromochloromethane and bromoform with densities at 2.45 and 2.89 g/cm$^3$ at room temperature, respectively, gives a larger relative density difference between the organic phase and the aqueous phase resulting in a phase separation that will occur on standing in under 1 minute.

Suitable solvents with densities above 2.0 g/cm$^3$ at room temperature include but are not limited to bromoform, dibromochloromethane, iodobromomethane, diiodomethane, dibromomethane, iodochloromethane, dibromoethane, 1,1,2,2-tetrabromoethane or 1,3-diiodopropane. Suitable solvents with densities above 2.4 g/cm$^3$ at room temperature include bromoform, dibromochloromethane, iodobromomethane, diiodomethane, dibromomethane, iodochloromethane, 1,1,2,2-tetrabromoethane or 1,3-diiodopropane. In certain embodiments mixtures of the aforementioned solvents may be used. In instances where fast separation at less hazardous conditions is pursued, a suitable organic solvent may be selected from the group consisting of dibromochloromethane, dibromomethane, iodochloromethane or 1,3-diiodopropane.

After standing, the extraction solution will have separated into two sharply defined phases with any precipitated or insoluble material present at the interphase. Either one or both phases may be used to further isolate desired target molecules including nucleic acids in total, certain fractions thereof (e.g. genomic DNA or total RNA etc.) and/or proteins. Methods of extracting DNA, RNA and proteins from a single sample are e.g. described in U.S. Pat. No. 5,346,994 or U.S. publication number 2014/0308670 A1. In many instances, the upper aqueous phase will contain the desired nucleic acid which may then be removed.

If needed, the extracted nucleic acid may be further processed by known methods in the art to concentrate and/or further purify the sample. The methods may include one or more of, alcohol precipitation, anion exchange chromatography, silica based column or membrane protocols, bead based protocols and treatment with DNAse or RNAse.

Example 1: Bead-Based Separation of Extracted Nucleic Acids

Figure 3:
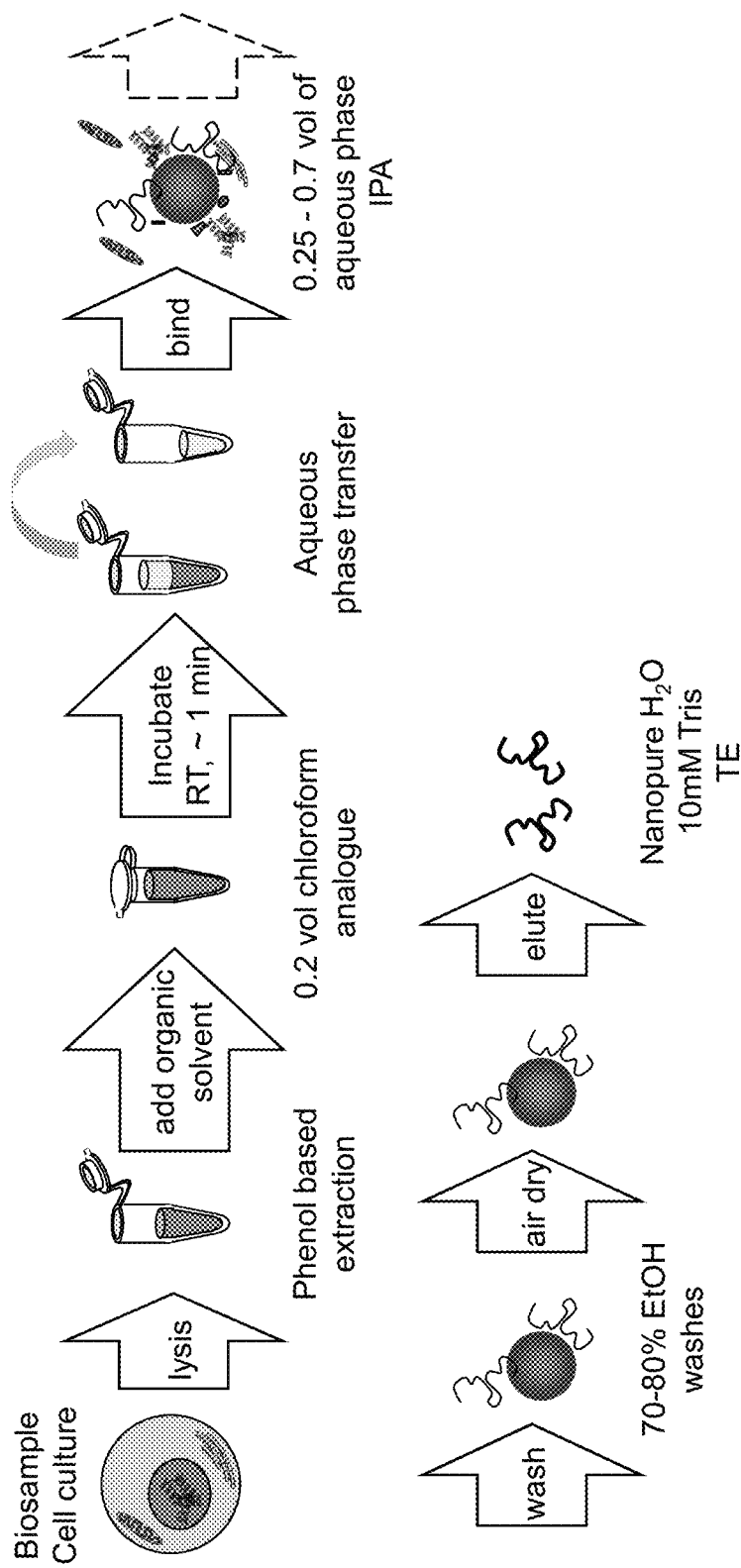
FIG. 3 shows an exemplary extraction workflow according to methods presented herein using bead-based nucleic acid separation.

An exemplary workflow using organic solvents according to the invention is illustrated in FIG. 3. Following lysis of a biological sample (e.g. cultured cells) and phenol-based extraction, 0.2 vol of a high density chloroform analogue (such as e.g. dibromochloromethane) is added and the sample is thoroughly mixed. The sample is allowed to stand at room temperature (RT) for about 1 minute to achieve phase separation. The upper aqueous phase containing the target nucleic acid is then transferred to another cup. The contained nucleic acid is precipitated on magnetic beads in the presence of 0.7 vol isopropyl alcohol (IPA) and optionally comprising 0.8 M sodium citrate or 1.2 M sodium chloride. The bead-bound nucleic acids are then washed using 70-80% ethanol and air-dried, before the nucleic acid is eluted in Nanopure H$_2$O, 10 mM Tris EDTA buffer.

Example 2: Isolation of Total RNA from Cultured Cells

To 1 million freshly harvested culture cells (volume ~100 µl) was added 10 volumes (1,000 µl) TRIZOL™ reagent. The solution was mixed by pipette until dissolved followed by incubation on a roller at RT for 5 minutes. Dibromochloromethane (0.2 volumes) was then added and mixed for 10 seconds followed by incubation on a roller for 2 minutes. The phases were then allowed to separate by standing the tube on the bench for 1 minute.

The upper aqueous phase was then transferred to a fresh tube and an equal volume of isopropyl alcohol added followed by brief mixing. Next, 50 microliters of DYNABEADS™ MYONE™ SILANE (40 mg/ml) were added and mixed for 10 seconds followed by incubation on a roller for 3 minutes. The beads were then washed using magnetic separation with 2×500 µl 75% ethanol solution. The bead pellet was allowed to air dry on the magnet for 10 mins after the final wash. The RNA was then eluted from the beads by suspending in elution buffer and incubating for 2 minutes at RT. The supernatant containing the total RNA was then transferred to a fresh tube.

In a second study, chloroform analogs were carried through the herein-described "no-spin" phenol-based methods and compared to the use of chloroform both in a "no-spin" phenol-based and in a traditional phenol-based centrifugation method. Two extractions were carried out per test control or test analog and each was carried out on 2×10$^6$ Jurkat cells in 150 microliters.

The protocol followed for this second study was as follows and results are presented in Table 2. TRIZOL™ reagent (1 ml, Thermo Fisher Scientific, Inc.) was added to freshly harvested cultured cells (2×10$^6$ cells) and the mixture pipetted until fully dissolved. The sample was then left to incubate at room temperature for 5 minutes. Chloroform or a chloroform analog (Table 2) (200 microliters) was added, the tube was shaken for 15 seconds, pictures were taken of the phase separation status versus time (0 sec, 1 min, 2 min, 5 min, 10 min, and at 15 min), and a record was made of the ease of aqueous phase transfer and whether phenol was carried over in the aqueous phase. Instead of standing for 5 minutes, the control chloroform samples (labeled "chloroform (spun, i.e., centrifuged)" in Table 2) were incubated at room temperature for 2 minutes, and then centrifuged for 5 min at 14000×g.

As stated above, all samples for this second study were kept on ice for 30 min prior to bead binding in order to visually record the extent of Trizol carryover to the aqueous phase.

The upper aqueous phase (500 microliters) of each sample was transferred to a fresh tube, and the following additions were made to the tube: DYNABEADS™ MYONE™ Silane bead suspension (25 microliters, Life Technologies, Inc. 40 mg/ml), 250 microliters of isopropanol, and a NaCl/NaCitrate solution (1.2 M NaCl+0.8 M NaCitrate, 500 microliters). The tube was vortexed for 30 seconds and then incubated on a roller for 10 minutes.

The beads were then washed using magnetic separation with 2×500 µl 75% ethanol solution. The bead pellet was allowed to air dry on the magnet for 10 min after the final wash. The RNA was then eluted from the beads by suspending in elution buffer and incubating for 2 minutes at RT. Elution may also occur at, for example, 50° C. The supernatant containing the total RNA was then transferred to a fresh tube and analyzed for recovery and purity using the SyBR Safe RNA analysis kit, a NANODROP™ spectrophotometer, and/or the Quant-iT Protein Assay Kit (all from Thermo Fisher Scientific Inc.).

Table 2 tabulates the density of chloroform and chloroform analogs used in this study (the density values were rounded to two significant digits as for Table 1), the phase separation status at designated times after addition of chloroform or the analog as visually observed from pictures taken beginning at zero seconds, characteristics of aqueous phase transfer, and descriptions of RNA recovery and purity for each. The centrifuged chloroform sample provided a control for comparison to the test samples and was characterized as providing a quick and easy transfer of the aqueous phase with no phenol carryover and average RNA recovery and purity.

When compared with the centrifuged chloroform control, the no-spin test samples with chloroform and 1-bromo-3-chloropropane had micelles present after 15 minutes of standing, the organic phase was easily disturbed and carryover of phenol occurred. The recovery and purity of RNA was no better or no worse than that of the centrifuged samples. Chloroform and 1-bromo-3-chloropropane have densities less than about 1.9 g/cm$^3$.

The phase separation analysis for those analogs having a density of greater than about 1.9 g/cm$^3$ and less than about 2.0 g/cm$^3$ indicated the presence of fewer micelles at the interface after 15 minutes as compared to the phase separation analysis for chloroform and 1-bromo-3-chloropropane. For these test samples, the organic phase was easily disturbed and phenol carry-over occurred. The recovery and purity of RNA was no better or no worse than that of the centrifuged samples.

The phase separation analysis for those analogs having a density of greater than about 2.0 g/cm$^3$ provided distinct phases within 1, 2, or 5 minutes with a quick and easy aqueous phase transfer and no phenol carryover (Table 2). For these reasons, these solvents would be most useful for automated procedures. Also, for these test analogs, the RNA recovery and RNA purity was equal to or better than that provided by chloroform. The highest purity was achieved using chloroiodomethane followed by dibromochloromethane and both achieved a RNA purity that surpassed the centrifuged chloroform sample.

At a density of 3.325 g/cm$^3$, the diiodomethane extraction provided three phases, the organic phase was easily disturbed, phenol carry-over occurred, and RNA purity was worse than all other test samples, including the chloroform control. However, recovery of RNA was the highest of all test samples; therefore, where recovery is of utmost importance, use of this organic solvent may be considered.

Clause 1: A method for the extraction of nucleic acid molecules from a biological sample comprising: a) adding an extraction solution to a biological sample, b) mixing the solution until the sample is dissolved, c) adding an organic solvent to the extraction solution, d) vigorously mixing the extraction solution, e) allowing the extraction solution to stand for up to one minute such that an aqueous phase and an organic phase are formed and the phases are fully separated from each other; and f) removing the upper aqueous phase containing the nucleic acid.

Clause 2: The method of clause 1, wherein the density of the organic solvent at room temperature is greater than or at least about 1.9 g/cm$^3$ and wherein the melting point of the solvent is less than or equal to 15° C.

Clause 3: The method of any of the preceding clauses, further comprising: g) processing the aqueous phase by one or more of alcohol precipitation, anion exchange chromatography, silica based chromatography, bead based protocols, treatment with DNAse and treatment with RNAse, and optionally further processing the organic phase to isolate nucleic acids or proteins.

Clause 4: The method of any of the preceding clauses, wherein the pH of the extraction solution is controlled using a buffer.

Clause 5: A composition comprising: a) a biological sample, b) a phenol based extraction solution; and c) an organic solvent having a density at room temperature that is greater than or at least about 1.9 g/cm$^3$ with a melting point of less than or equal to 15° C. and a boiling point greater than about 50° C.

TABLE 2

| Compound | Density (g/cm$^3$) | Phase separation status | Ease of phase transfer | RNA recovery | RNA purity |
|---|---|---|---|---|---|
| Chloroform (spun, i.e., centrifuged) | 1.49 | control (spun, i.e., centrifuged) | quick and easy, no phenol carry-over | average | average |
| Chloroform | 1.49 | still micelles after 15 min | organic phase easily disturbed, phenol carry-over | average | average |
| 1-Bromo-3-chloropropane | 1.59 | still micelles after 15 min | organic phase easily disturbed, phenol carry-over | average | average |
| 1,2 Dibromopropane | 1.94 | still micelles after 15 min, but less than for chloroform, 1-bromo-3-chloropropane, and 1,3 dibromopropane | organic phase easily disturbed, phenol carry-over | average | average |
| 1,3 Dibromopropane | 1.99 | still micelles after 15 min, but less than for chloroform, and 1-bromo-3-chloropropane | organic phase easily disturbed, phenol carry-over | average | average |
| Chloroiodomethane | 2.42 | distinct phase after 5 min | quick and easy, no phenol carry-over | higher | highest |
| Dibromochloromethane | 2.45 | distinct phases after 1-2 min | quick and easy, no phenol carry-over | higher | higher |
| 1,3 Diiodopropane | 2.58 | distinct phases after 1-2 min | quick and easy, no phenol carry-over | average | average |
| Bromoform | 2.89 | distinct phases after 1-2 min | quick and easy, no phenol carry-over | average | average |
| 1,1,2,2, Tetrabromoethane | 2.97 | distinct phases after 1-2 min | quick and easy, no phenol carry-over | higher | average |
| Diiodomethane | 3.33 | ~5 min; three phases | organic phase easily disturbed, phenol carry-over | highest | worst |

The invention being thus described, one skilled in the art would recognize that the invention may be varied in many ways. Such variations are not to be regarded as a departure from the spirit and scope of the invention, and all such modifications as would be obvious to one of ordinary skill in the art are intended to be included within the scope of the following claims.

The invention is further represented by the following clauses:

Clause 6: The method of any of clauses 1 to 4 or the composition of clause 5, wherein the density of the organic solvent at room temperature is greater than or at least about 2.0 g/cm$^3$ and optionally, greater than or at least about 2.4 g/cm$^3$.

Clause 7: The method of any of clauses 1 to 4 or 6 or the composition of clause 5 or 6, wherein the organic solvent is a halo substituted alkyl compound.

Clause 8: The method of any of clauses 1 to 4, 6 or 7, or the composition of any of clauses 5 to 7, wherein the organic solvent is selected from the group consisting of bromoform, dibromochloromethane, dibromomethane, iodochloromethane, 1,3-dibromopropane, 1,2-dibromopropane and 1,3-diiodopropane.

Clause 9: The method of any of clauses 1 to 4 or 6 to 8, or the composition of any of clauses 5 to 8, wherein the extraction solution further comprises a chaotropic agent.

Clause 10: The method or the composition of clause 9, wherein the chaotropic agent is guanidinium or a guadinium salt.

Clause 11: The method of any of clauses 1 to 4 or 6 to 10, or the composition of any of clauses 5 to 10, wherein the extraction solution further comprises a thiocyanate compound, optionally wherein the thiocyanate compound is ammonium thiocyanate or sodium thiocyanate.

Clause 12: The method of any of clauses 1 to 4 or 6 to 11, or the composition of any of clauses 5 to 11, wherein the pH of the extraction solution is between 3.5 and 8, or below 5.

Clause 13: The method of any of clauses 1 to 4 or 6 to 12, or the composition of any of clauses 5 to 12, wherein the extraction solution further comprises a solubilization reagent, optionally wherein the solubilization reagent is glycerol.

Clause 14: The method of any of clauses 1 to 4 or 6 to 13, wherein the biological sample is selected from cultured cells, tissues including animal and plant tissue, FFPE, optionally homogenized, or from biological fluids including blood, urine, saliva, semen, and spinal fluid.

Clause 15: Use of an organic solvent having a density at room temperature of at least about 1.9 g/cm$^3$, preferably at least about 2.0 g/cm$^3$, more preferably at least about 2.4 g/cm$^3$ for phase separation in phenol-based extraction of nucleic acids from a biological sample.

Clause 16: The use according to clause 15, wherein the biological sample is selected from cultured cells, tissues including animal and plant tissue, FFPE, optionally homogenized, or from biological fluids including blood, urine, saliva, semen, and spinal fluid, and the nucleic acid is selected from genomic DNA or RNA.

Clause 17: The use according to clause 15 or 16, wherein the organic solvent is selected from the group consisting of bromoform, dibromochloromethane, dibromomethane, iodochloromethane, 1,3-dibromopropane, 1,2-dibromopropane and 1,3-diiodopropane.

Clause 18: A method for the extraction of nucleic acid molecules from a biological sample comprising: a) mixing the biological sample and a phenol-based extraction solution to form a dissolved sample, b) mixing an organic solvent with the dissolved sample to form a mixture, wherein the organic solvent is a halo-substituted alkyl compound having one to three carbon atoms, wherein the organic solvent has a density at room temperature of greater than or at least about 1.9 g/cm$^3$, and wherein the organic solvent has a melting point of less than or equal to 15° C., c) allowing the mixture to stand for an amount of time to achieve separation of an aqueous phase and an organic phase; and d) removing the aqueous phase containing the nucleic acid.

The method of clause 18, wherein the organic solvent has a density that is ≥1.9 g/cm$^3$ and <4.0 g/cm$^3$, or ≥2.0 g/cm$^3$ and <4.0 g/cm$^3$, or ≥2.4 g/cm$^3$ and <4.0 g/cm$^3$ selected from those listed in Table 1 or Table 2, or a mixture thereof.

The method of clause 18, wherein the organic solvent has a density that is ≥1.9 g/cm$^3$ and ≤3.3 g/cm$^3$, or ≥2.0 g/cm$^3$ and ≤3.3 g/cm$^3$, or ≥2.4 g/cm$^3$ and ≤3.3 g/cm$^3$ selected from those listed in Table 1 or Table 2, or a mixture thereof.

The method of clause 24, wherein the organic solvent has a density that is ≥1.9 g/cm$^3$ and <3.3 g/cm$^3$, or ≥2.0 g/cm$^3$ and <3.3 g/cm$^3$, or ≥2.4 g/cm$^3$ and <3.3 g/cm$^3$ selected from those listed in Table 1 or Table 2, or a mixture thereof.

The invention claimed is:

1. A method for the extraction of nucleic acid from a biological sample comprising:
   a) adding a phenol-based extraction solution to a biological sample,
   b) mixing the solution until the sample is dissolved,
   c) adding an organic solvent to the extraction solution wherein the organic solvent is dibromochloromethane, iodochloromethane, or mixtures thereof,
   d) vigorously mixing the extraction solution,
   e) allowing the extraction solution to stand for a sufficient amount of time such that an aqueous phase and an organic phase are formed and the phases are fully separated from each other; and
   f) removing the upper aqueous phase containing the nucleic acid.

2. The method of claim 1, further comprising:
   g) processing the aqueous phase by one or more of alcohol precipitation, anion exchange chromatography, silica based chromatography, bead based protocols, and treatment with DNAse.

3. The method of claim 1, further comprising:
   g) processing the aqueous phase by one or more of alcohol precipitation, anion exchange chromatography, silica base chromatography, bead based protocols and treatment with RNAse.

4. The method of claim 1, wherein the extraction solution further comprises a chaotropic agent.

5. The method of claim 4, wherein the chaotropic agent is a guanidinium salt.

6. The method of claim 1, wherein the extraction solution further comprises a thiocyanate compound.

7. The method of claim 6, wherein the thiocyanate compound is selected from ammonium thiocyanate and sodium thiocyanate.

8. The method of claim 1, wherein the pH of the extraction solution is acidic thereby allowing for preferential isolation of RNA from the upper aqueous phase.

9. The method of claim 1, wherein the pH of the extraction solution is between 3.5 and 8.

10. The method of claim 1, wherein the extraction solution further comprises a solubilization reagent wherein the solubilization reagent is glycerol.

11. A composition comprising:
    a) a biological sample,
    b) a phenol based extraction solution; and
    c) an organic solvent wherein the organic solvent is dibromochloromethane, iodochloromethane, or mixtures thereof.

12. The composition of claim 11, wherein the extraction solution further comprises a chaotropic agent.

13. The composition of claim 12, wherein the chaotropic agent is a guanidinium ion or a guanidinium salt.

14. The composition of claim 11, wherein the extraction solution further comprises a thiocyanate compound.

15. The composition of claim 14, wherein the thiocyanate compound is ammonium thiocyanate or sodium thiocyanate.

16. The composition of claim 11, wherein the pH of the extraction solution is between 3.5 and 8.

17. The composition of claim 16, wherein the extraction solution further comprises a solubilization reagent wherein the solubilization reagent is glycerol.

18. A method for the extraction of nucleic acid from a biological sample comprising:
   a) mixing the biological sample and a phenol-based extraction solution to form a dissolved sample,
   b) mixing an organic solvent with the dissolved sample to form a mixture,
      wherein the organic solvent is dibromochloromethane, iodochloromethane, or mixtures thereof,
   c) allowing the mixture to stand for an amount of time to achieve separation of an aqueous phase and an organic phase; and
   d) removing the aqueous phase containing the nucleic acid.

19. The method of claim 18 wherein the organic solvent is dibromochloromethane.

20. The method of claim 18 wherein the organic solvent is iodochloromethane.

\* \* \* \* \*

UNITED STATES PATENT AND TRADEMARK OFFICE
CERTIFICATE OF CORRECTION

PATENT NO. : 10,787,659 B2
APPLICATION NO. : 16/137448
DATED : September 29, 2020
INVENTOR(S) : Darren Ellis and Hannah Lindstroem Page 1 of 1

It is certified that error appears in the above-identified patent and that said Letters Patent is hereby corrected as shown below:

In the Claims

Column 14, Claim 13, Line 58, please delete the phrase "a guanidinium ion or".

Signed and Sealed this
Twenty-second Day of December, 2020

Andrei Iancu
*Director of the United States Patent and Trademark Office*